US00PP28494P3

(12) United States Plant Patent
Heuger

(10) Patent No.: US PP28,494 P3
(45) Date of Patent: Oct. 3, 2017

(54) ***ARGYRANTHEMUM* PLANT NAMED 'SUN 440'**

(50) Latin Name: *Argyranthemum frutescens*
Varietal Denomination: SUN 440

(71) Applicant: Josef Heuger, Glandorf (DE)

(72) Inventor: Josef Heuger, Glandorf (DE)

( * ) Notice: Subject to any disclaimer, the term of this patent is extended or adjusted under 35 U.S.C. 154(b) by 41 days.

(21) Appl. No.: 14/998,614

(22) Filed: Jan. 23, 2016

(65) Prior Publication Data

US 2017/0215320 P1 Jul. 27, 2017

(51) Int. Cl.
*A01H 5/02* (2006.01)

(52) U.S. Cl.
USPC ..... Plt./406

(58) Field of Classification Search
USPC ..... Plt./406
See application file for complete search history.

*Primary Examiner* — Susan McCormick Ewoldt
(74) *Attorney, Agent, or Firm* — C. A. Whealy

(57) ABSTRACT

A new and distinct cultivar of *Argyranthemum* plant named 'SUN 440', characterized by its uniformly mounded plant habit; freely branching habit; freely flowering habit; single-type inflorescences with white-colored ray florets; and good garden performance.

2 Drawing Sheets

Botanical designation: *Argyranthemum frutescens*.
Cultivar denomination: 'SUN 440'.

BACKGROUND OF THE INVENTION

The present invention relates to a new and distinct cultivar of *Argyranthemum* plant, botanically known as *Argyranthemum frutescens* and hereinafter referred to by the cultivar name 'SUN 440'.

The objective of the breeding program is to create new *Argyranthemum* plants with attractive ray and disc floret colors and good garden performance and pest resistance.

The new *Argyranthemum* plant originated from a cross-pollination made by the Inventor in August, 2011 in Glandorf, Germany of two unnamed seedling selections of *Argyranthemum frutescens*, not patented. The new *Argyranthemum* plant was discovered and selected by the Inventor as a single flowering plant from within the progeny of the stated cross-pollination in a controlled greenhouse environment in Glandorf, Germany in July, 2012.

Asexual reproduction of the new *Argyranthemum* plant by vegetative tip cuttings was first conducted in Glandorf, Germany in February, 2013. Asexual reproduction by cuttings has shown that the unique features of this new *Argyranthemum* plant are stable and reproduced true to type in successive generations.

SUMMARY OF THE INVENTION

Plants of the new *Argyranthemum* have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of the new *Argyranthemum* plant. These characteristics in combination distinguish 'SUN 440' as a new and distinct *Argyranthemum* plant:

1. Uniformly mounded plant habit.
2. Freely branching habit.
3. Freely flowering habit.
4. Single-type inflorescences with white-colored ray florets.
5. Good garden performance.

Plants of the new *Argyranthemum* differ from plants of the parent selections primarily in uniformity as plants of the new *Argyranthemum* are more uniformly mounding than plants of the parent selections.

Plants of the new *Argyranthemum* can be compared to plants of *Argyranthemum frutescens* 'SUN 160', not patented. In side-by-side comparisons conducted in Glandorf, Germany, plants of the new *Argyranthemum* differed primarily from plants of 'SUN 160' in ray floret color as plants of 'SUN 160' have red-colored ray florets.

BRIEF DESCRIPTION OF THE PHOTOGRAPHS

The accompanying photographs illustrate the overall appearance of the new *Argyranthemum* showing the colors as true as it is reasonably possible to obtain in colored reproductions of this type. Colors in the photographs may differ slightly from the color values cited in the detailed botanical description which accurately describe the colors of the new *Argyranthemum* plant.

The photograph on the first sheet comprises a side perspective view of a typical flowering plant of 'SUN 440' grown in a container.

The photograph on the second sheet is a close-up view of a typical flowering plant of 'SUN 440'.

DETAILED BOTANICAL DESCRIPTION

The aforementioned photographs and following observations and measurements describe plants grown during the spring and early summer in 9-cm containers in a glass-covered greenhouse in Glandorf, Germany and under cultural practices typical of commercial potted *Argyranthemum* production. During the production of the plants, day temperatures ranged from 14° C. to 28° C., night temperatures ranged from 10° C. to 18° C. and light levels ranged from 25 klux to 90 klux. Plants were pinched one time five weeks after planting and were 2.5 months old when the photographs and description were taken. In the following description, color references are made to The Royal Horticultural Society Colour Chart, 2007 Edition, except where general terms of ordinary dictionary significance are used.

Botanical classification: *Argyranthemum frutescens* 'SUN 440'.

Parentage:

*Female, or seed, parent*.—Unnamed seedling selection of *Argyranthemum frutescens*, not patented.

*Male, or pollen, parent*.—Unnamed seedling selection of *Argyranthemum frutescens*, not patented.

Propagation:

*Type*.—Terminal cuttings.

*Time to initiate roots, summer*.—About 8 to 10 days at temperatures about 18° C. to 24° C.

*Time to initiate roots, winter*.—About 10 to 15 days at temperatures about 14° C. to 18° C.

*Time to produce a rooted young plant, summer*.—About 14 to 16 days at temperatures about 18° C. to 24° C.

*Time to produce a rooted young plant, winter*.—About 16 to 20 days at temperatures about 14° C. to 18° C.

*Root description*.—Fine to medium in thickness, fibrous; typically white in color, actual color of the roots is dependent on substrate composition, water quality, fertilizer type and formulation, substrate temperature and physiological age of roots.

*Rooting habit*.—Moderate branching; medium density.

Plant description:

*Plant and growth habit*.—Herbaceous perennial; uniformly mounding plant habit; upright to broadly spreading form; overall shape, roughly flattened globular; moderately vigorous growth habit.

*Branching habit*.—Freely branching growth habit with about 23 lateral branches developing per plant; pinching enhances lateral branch development.

*Plant height*.—About 14.4 cm.

*Plant width*.—About 22.6 cm.

*Lateral branches*.—Length: About 6.1 cm. Diameter: About 3.5 mm. Internode length: About 1.4 cm. Strength: Strong; young stems, flexible. Texture: Smooth, glabrous. Luster: Slightly glossy. Color: Close to 137D.

Leaf description:

*Arrangement*.—Alternate, simple; sessile.

*Length*.—About 7.2 cm.

*Width*.—About 3.1 cm.

*Shape*.—Pinnatisect; in outline, narrowly obovate.

*Apex*.—Acute.

*Base*.—Cuneate.

*Margin*.—Deeply incised.

*Sinuses*.—Parallel to slightly divergent.

*Texture, upper and lower surfaces*.—Smooth, glabrous; leathery.

*Luster, upper and lower surfaces*.—Matte.

*Venation*.—Pinnate.

*Color*.—Developing leaves, upper surface: Close to 137C. Developing leaves, lower surface: Close to 138A to 138B. Fully expanded leaves, upper surface: Close to N137C; venation, close to 138B. Fully expanded leaves, lower surface: Close to 137C; venation, close to 138A.

Inflorescence description:

*Inflorescence form and arrangement*.—Single-type terminal and axillary inflorescences held above and beyond the foliar plane on strong peduncles; ray and disc florets arranged acropetally on a receptacle; inflorescences face mostly upright to outwardly.

*Flowering habit*.—Freely flowering habit with about 125 inflorescences developing per plant during the flowering season.

*Flowering season*.—Plants flower from spring to late summer in Germany; flowering continuous during this period.

*Inflorescence longevity*.—Inflorescences last about two to three weeks on the plant; inflorescences not persistent.

*Fragrance*.—Moderately fragrant.

*Inflorescence buds*.—Height: About 7 mm. Diameter: About 7 mm. Shape: Globular. Color: Towards the base, close to 144B; towards the apex, close to 199B; towards the margins, close to 166C.

*Inflorescence size*.—Diameter: About 4.5 cm. Depth (height): About 1.5 cm. Diameter of disc: About 1.3 cm. Receptacle diameter: About 5 mm. Receptacle height: About 4 mm.

*Ray florets*.—Quantity per inflorescence and arrangement: About 31 to 44 arranged in about three whorls. Length: About 2.2 cm. Width: About 6.5 mm. Shape: Oblanceolate. Apex: Emarginate to shallowly praemorse. Base: Attenuate. Margin: Entire. Texture, upper surface: Smooth, glabrous; velvety. Texture, lower surface: Glabrous; carinate. Luster, upper and lower surfaces: Slightly glossy. Color: When opening, upper surface: Close to NN155A to NN155B. When opening, lower surface: Close to NN155D. Fully opened, upper surface: Close to NN155D; color does not change with development. Fully opened, lower surface: Close to NN155D slightly tinged with close to 186D; color does not change with development.

*Disc florets*.—Quantity per inflorescence and arrangement: About 175 spirally arranged at center of receptacle. Length: About 5.5 mm. Diameter, apex: About 2 mm. Diameter, base: About 0.5 mm. Shape: Tubular with five free apical lobes. Apex: Acute. Texture, inner and outer surfaces: Smooth, glabrous. Luster, inner surface: Glossy. Luster, outer surface: Matte. Color, immature, inner and outer surfaces: Apex: Close to 200A. Mid-section and base: Close to 150D. Color, mature, inner and outer surfaces: Apex: Close to 175B. Mid-section and base: Close to 145D.

*Phyllaries*.—Quantity per inflorescence and arrangement: About 24 arranged in two whorls. Length: About 4 mm. Width: About 2.5 mm. Shape: Ovate. Apex: Praemorse. Base: Broadly cuneate. Margin: Entire. Texture, upper and lower surfaces: Smooth, glabrous; edges, papery. Luster, upper surface: Glossy. Luster, lower surface: Matte. Color, upper surface: Close to 144B to 144C; margins and papery edges, close to 199B. Color, lower surface: Close to 143B; margins and papery edges, close to 199B.

*Peduncles*.—Length, terminal peduncle: About 3.8 cm. Length, fourth peduncle: About 7.9 cm. Diameter:

About 2 mm. Angle: Terminal peduncle, erect; lateral peduncles, about 50° from branch axis. Strength: Strong. Texture: Slightly ribbed, glabrous. Luster: Slightly glossy. Color: Close to 137C.

*Reproductive organs*.—Androecium: Present on disc florets only. Filament length: About 1.5 mm. Anther length: About 1 mm. Anther shape: Lanceolate; basifixed. Anther color: Close to 14B. Pollen amount: Scarce to moderate. Pollen color: Close to 17B. Gynoecium: Present on both ray and disc florets. Pistil length: About 4 mm. Stigma shape: Decurrent. Stigma color: Close to 13A. Style length: About 3.5 mm. Style color: Close to 154B. Ovary color: Close to 145C.

*Seeds and fruits*.—Seed and fruit production has not been observed on plants of the new *Argyranthemum*.

Disease & pest resistance: Plants of the new *Argyranthemum* have not been shown to be resistant to pathogens and pests common to *Argyranthemum* plants.

Garden performance: Plants of the new *Argyranthemum* have been observed to have good garden performance and to tolerate rain, wind, high temperatures about 40° C. and to be hardy to USDA Hardiness Zone 9.

It is claimed:

1. A new and distinct *Argyranthemum* plant named 'SUN 440' as illustrated and described.

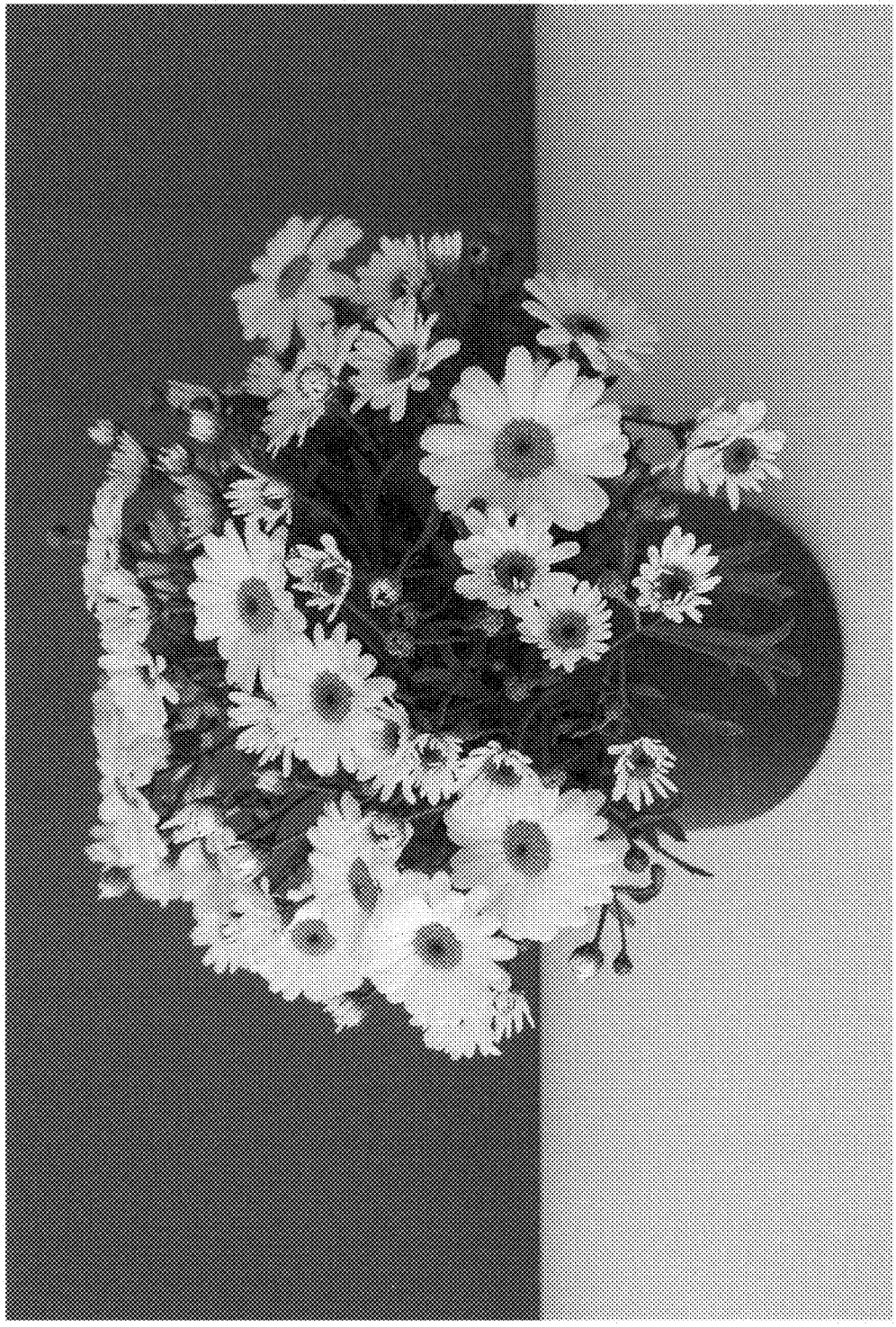

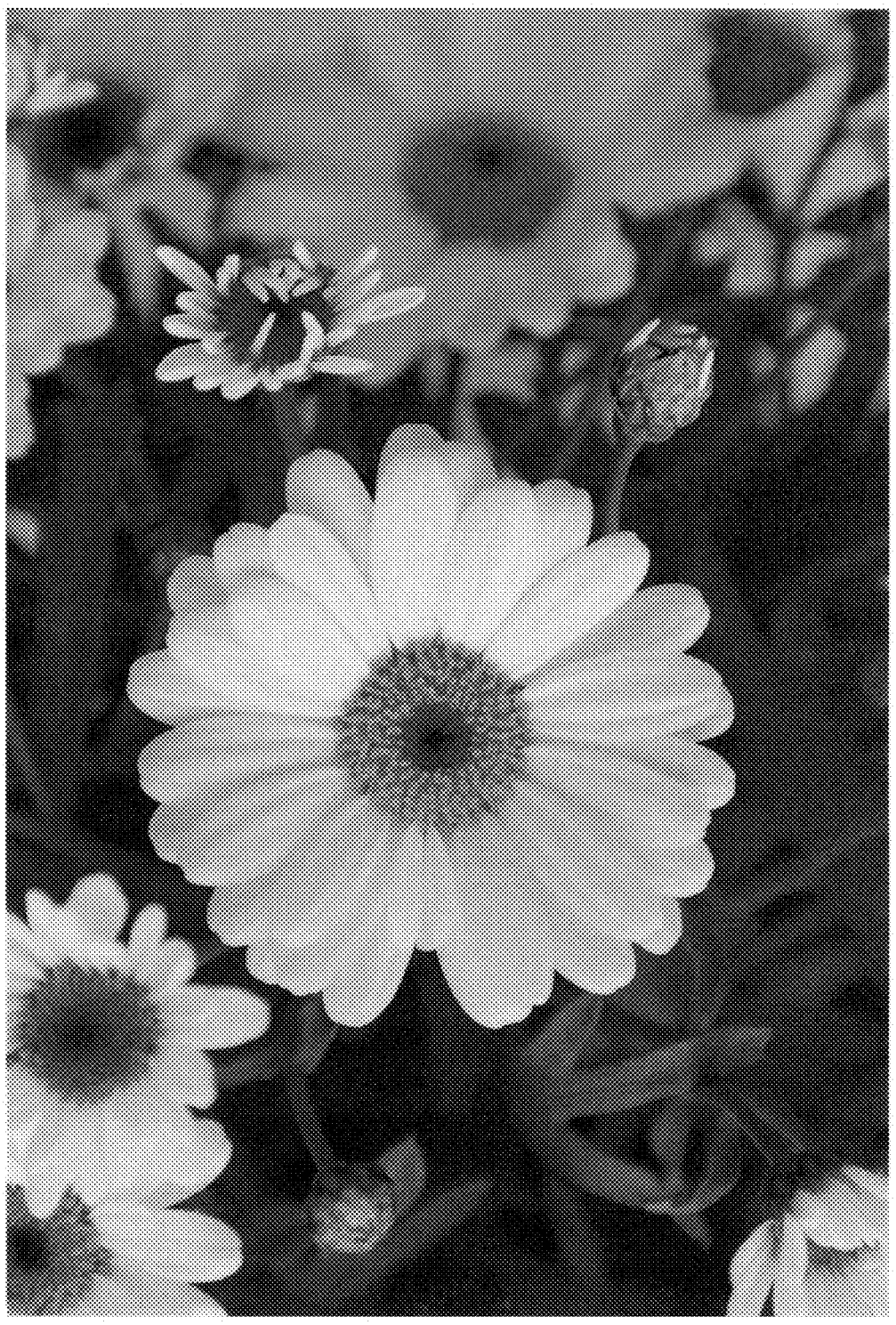

* * * * *